United States Patent [19]

Rosenberg et al.

[11] Patent Number: 5,354,561
[45] Date of Patent: Oct. 11, 1994

[54] PROCESS FOR PRODUCING SOLID ACTIVE SUBSTANCE FORMS AND PRODUCTS THEREOF

[75] Inventors: Joerg Rosenberg, Ludwigshafen, Fed. Rep. of Germany; Juergen Heberger, Schifferstadt, Fed. Rep. of Germany

[73] Assignee: Knoll AG, Ludwigshafen, Fed. Rep. of Germany

[21] Appl. No.: 920,555

[22] PCT Filed: Mar. 20, 1991

[86] PCT No.: PCT/EP91/00538
§ 371 Date: Aug. 19, 1992
§ 102(e) Date: Aug. 19, 1992

[87] PCT Pub. No.: WO91/14425
PCT Pub. Date: Oct. 3, 1991

[30] Foreign Application Priority Data

Mar. 29, 1990 [DE] Fed. Rep. of Germany ....... 4009984

[51] Int. Cl.$^5$ ................................................ A61K 9/14
[52] U.S. Cl. ..................................... 424/489; 424/485; 424/486; 424/450

[58] Field of Search ............... 424/486, 485, 489, 450; 524/733

[56] References Cited

U.S. PATENT DOCUMENTS

| 4,794,000 | 12/1988 | Ecanow | 424/457 |
| 4,963,367 | 10/1990 | Ecanow | 424/485 |
| 4,997,867 | 3/1991 | Jederstrom | 524/733 |
| 5,147,655 | 9/1992 | Ibsen | 424/489 |

FOREIGN PATENT DOCUMENTS

| 0274431 | 1/1988 | European Pat. Off. . |
| 3400106 | 7/1985 | Fed. Rep. of Germany . |

*Primary Examiner*—Thurman K. Page
*Assistant Examiner*—William E. Benston, Jr.
*Attorney, Agent, or Firm*—Keil & Weinkauf

[57] ABSTRACT

A process is described for the production of solid forms of active substances, which forms have good redispersibility in aqueous systems, which comprises mixing PEG and dextran with water and—if phase separation occurs—removing the upper phase, dissolving an active substance in the mixture, where appropriate adding a physiologically tolerated amphiphile, and subsequently removing the water.

3 Claims, No Drawings

PROCESS FOR PRODUCING SOLID ACTIVE SUBSTANCE FORMS AND PRODUCTS THEREOF

The present invention relates to a process for the production of solid forms of active substances, to the products obtained with the aid of this process, and to the use of these products for the production of drugs.

It is known that phase separation occurs when an aqueous solution of polyethylene glycol and a likewise aqueous solution of dextran are mixed. According to U.S. Pat. No. 4,794,000, the lower "colloid-rich" phase can be employed for formulating active substances, where appropriate after the addition of other auxiliaries such as lecithin. All the formulations described therein are, however, liquid drug forms, often highly viscous, and therefore disadvantageous, especially for oral administration forms. In addition, there must be expected to be, especially in the liquid state, considerable stability problems of a physical (phase separation, recrystallization etc.) and chemical nature (hydrolysis reactions, oxidations etc.).

All the auxiliaries employed for the formulation (polyethylene glycol 6000, dextran 40 and egg lecithin) display wax-like, sticky properties and therefore give rise to problems in the formulation of active substances. In their turn, active substances may have a consistency which makes pharmaceutical processing difficult.

A very straightforward and efficient process for the production of solid forms of active substances has now been found.

The invention relates to a process for the production of solid forms of active substances, which forms have good redispersibility in aqueous systems, which comprises mixing PEG and dextran with water and—if phase separation occurs—removing the upper phase, dissolving an active substance in the mixture, where appropriate adding a physiologically tolerated amphiphile, and subsequently removing the water.

Particularly suitable active substances are those which are soluble in water. Suitable as PEG (=polyethylene glycol) are, in particular, those with a molecular weight of 2,000 to 20,000, e.g. PEG 4,000 and PEG 10,000. PEG 6,000 is very particularly suitable.

It is advisable to add an amphiphile to the mixture after adding the active substance. Suitable as amphiphile are all which are physiologically tolerated, such as lipids which form bilayer membranes. Examples of these are phospholipids or synthetic amphiphiles. Examples of synthetic amphiphiles are described in EP-A 331,092. Very particularly suitable are phospholipids, preferably lecithins such as egg lecithin, soybean lecithin and synthetic phospholipids.

The removal of the water from the substance mixture is carried out, for example, by spray-drying or freeze-drying.

The invention also relates to the active substance form which is obtained by the described process and which can be processed in a known manner to a finished drug form. The active substance form is very suitable for the production of instant forms, for example for injection preparations and for drinkable solutions, but also, furthermore, in particular for solid oral drug forms (after the powder has been packed into hard gelatin capsules or compressed to tablets).

It was surprising that defined mixtures of these sticky, wax-like auxiliaries yield, even in combination with various active substances after removal of the water, a hard, brittle and easily powdered composition which is free-flowing and therefore can, for example, be packed without problems into hard gelatin capsules. These product properties were not predictable because of the consistency of the starting materials. It was furthermore surprising that transparent films are formed on removal of the water when the solution is, for example, dried in a shallow dish. The films adhere extremely poorly to glass and become detached from the substrate without further treatment. This property was not predictable either, because of the consistency of the starting materials. The transparency of the films containing active substance suggests that the active substance is present in molecular disperse form, in the form of a quasi "solid solution".

The solid forms of active substances produced as described in the present invention can, surprisingly, easily be redispersed in water.

The examples which follow illustrate the invention:

EXAMPLE 1 a) Preparation of the Colloid-Rich Lower Phase 50.0 g of dextran 40 and 15.0 g of polyethylene glycol 6000 were mixed with 200 ml of distilled water. Stirring was continued at 80° C until both substances had completely dissolved. After transfer into a separating funnel, the mixture was allowed to cool to room temperature, and then the water-clear lower phase was separated off (about 160 ml), the upper phase was discarded.

b) Formulation with Lecithin and Active Substance 20.0 ml of the solution obtained in Example 1 were mixed at 65° C. with 0.5 g of verapamil hydrochloride. After the active substance had dissolved, 1.0 g of lecithin E 100 (egg lecithin supplied by Lipoid KG, Ludwigshafen) was dissolved by stirring, likewise at 65° C., until a clear honey-like composition was formed.

c) Drying of the Formulation

Most of the water was removed from the formulation obtained in Example 2 in a round-bottom flask on a rotary evaporator (60° C. bath temperature, water pump vacuum). The contents of the flask were subsequently dried in a desiccator over drying agent ($P_4O_{10}$) in vacuo for 24 h to complete removal of the water. The remaining composition was finally powdered in a mortar.

Yield: 6.84 g.

EXAMPLE 2

Preparation was carried out as indicated in Example 1 but with 1.0 g of verapamil hydrochloride.
Yield: 7.5 g.

EXAMPLE 3

Preparation was carried out as indicated in Example 1 but with 0.5 g of anipamil hydrochloride.
Yield: 6.75 g.

EXAMPLE 4

Preparation was carried out as indicated in Example 1 but with 1.0 g of anipamil hydrochloride.
Yield: 7.08 g.

EXAMPLE 5

Preparation was carried out as indicated in Example 1 but with 0.5 g of gallopamil hydrochloride.

Yield: 7.01 g.

EXAMPLE 6

Preparation was carried out as indicated in Example 1 but with 1.0 g of gallopamil hydrochloride.

Yield: 7.33 g.

EXAMPLE 7

Preparation was carried out as indicated in Example 1 but with 0.5 g of (S)-emopamil hydrochloride.

Yield: 7.3 g.

EXAMPLE 8

Preparation was carried out as indicated in Example 1 but with 1.0 g of (S)-emopamil hydrochloride.

Yield: 7.6 g.

EXAMPLE 9

Preparation was carried out as indicated in Example 1 but with 2.0 g of (S)-emopamil hydrochloride.

Yield: 8.4 g.

We claim:

1. A process for the production of solid forms of water-soluble active substances of drugs, which forms have good redispersibility in aqueous systems, which comprises mixing PEG and dextran with water, removing the upper phase from the resulting two-phase mixture, dissolving the water-soluble active substance in the water-clear lower phase which was formed, adding a physiologically tolerated amphiphile and subsequently removing the water.

2. A solid form of an active substance, prepared by the process of claim 1.

3. A drug composition comprising the active substance of claim 2.

* * * * *